(12) United States Patent
Lee et al.

(10) Patent No.: US 9,324,035 B2
(45) Date of Patent: Apr. 26, 2016

(54) APPARATUS AND METHOD FOR PREDICTING POTENTIAL CHANGE OF CORONARY ARTERY CALCIFICATION (CAC) LEVEL

(71) Applicants: Samsung Electronics Co., Ltd., Suwon-si (KR); Samsung Life Welfare Foundation, Seoul (KR)

(72) Inventors: Ji-Hyun Lee, Hwaseong-si (KR); Hye-Jin Kam, Seongnam-si (KR); Ha-Young Kim, Hwaseong-si (KR); Sang-Hyun Yoo, Seoul (KR); Yoonho Choi, Seoul (KR); Mira Kang, Seoul (KR); Jeongeuy Park, Seoul (KR); Jidong Sung, Seoul (KR); Heeyoung Shin, Seoul (KR); Sungwon Cho, Seoul (KR); Soojin Cho, Seoul (KR)

(73) Assignees: Samsung Electronics Co., Ltd., Suwon-si (KR); Samsung Life Welfare Foundation, Seoul (KR)

( * ) Notice: Subject to any disclaimer, the term of this patent is extended or adjusted under 35 U.S.C. 154(b) by 425 days.

(21) Appl. No.: 13/835,855

(22) Filed: Mar. 15, 2013

(65) Prior Publication Data

US 2013/0275347 A1 Oct. 17, 2013

(30) Foreign Application Priority Data

Mar. 15, 2012 (KR) .................. 10-2012-0026812

(51) Int. Cl.
*G06N 99/00* (2010.01)
*G06F 19/00* (2011.01)
(52) U.S. Cl.
CPC ............ *G06N 99/005* (2013.01); *G06F 19/345* (2013.01); *G06F 19/3431* (2013.01)

(58) Field of Classification Search
None
See application file for complete search history.

(56) References Cited

U.S. PATENT DOCUMENTS

| 6,233,304 | B1 | 5/2001 | Hu et al. |
| 6,796,946 | B2 | 9/2004 | Ogura et al. |
| 6,923,771 | B2 | 8/2005 | Ogura et al. |
| 7,907,766 | B2 | 3/2011 | Lehel et al. |
| 2003/0212334 | A1 | 11/2003 | Ogura et al. |

(Continued)

FOREIGN PATENT DOCUMENTS

| EP | 1 684 202 A1 | 7/2006 |
| JP | 2002-24401 A | 1/2002 |

(Continued)

OTHER PUBLICATIONS

Matsuoka et alia. Impact of High Coronary Artery Calcification Score (CACS) on Survival in Patients on Chronic Hemodialysis. Clin Exp Nephrol (2004) 8:54-58.*

(Continued)

*Primary Examiner* — Stanley K Hill
*Assistant Examiner* — Robert H Bejcek, II
(74) *Attorney, Agent, or Firm* — NSIP Law

(57) ABSTRACT

An apparatus and a method predict a patient's potential change of Coronary Artery Calcification (CAC) level using various risk factors including a Coronary Artery Calcification Score (CACS). The apparatus includes a receiving unit, a cluster determining unit, a risk factor score extracting unit, a prediction model storage unit, a prediction model learning unit, and a predicting unit, and the method includes a receiving process, a risk factor score extracting process, and an operation performing process.

14 Claims, 7 Drawing Sheets

(56) References Cited

U.S. PATENT DOCUMENTS

| | | | |
|---|---|---|---|
| 2004/0162494 | A1 | 8/2004 | Ogura et al. |
| 2005/0059876 | A1* | 3/2005 | Krishnan et al. ............... 600/407 |
| 2009/0204338 | A1 | 8/2009 | Nielsen et al. |
| 2010/0125202 | A1 | 5/2010 | Lee et al. |
| 2010/0278405 | A1 | 11/2010 | Kakadiaris et al. |
| 2011/0257545 | A1 | 10/2011 | Suri |
| 2012/0283530 | A1* | 11/2012 | Maynard et al. ............... 600/316 |

FOREIGN PATENT DOCUMENTS

| | | | |
|---|---|---|---|
| JP | 2003-310601 | A | 11/2003 |
| JP | 2006-109959 | A | 4/2006 |
| KR | 2000-0036350 | A | 7/2000 |
| KR | 10-0865647 | B1 | 10/2008 |
| KR | 10-2009-0041817 | A | 4/2009 |
| KR | 10-0935610 | B1 | 1/2010 |
| KR | 10-2010-0056253 | A | 5/2010 |
| KR | 10-2010-0133972 | A | 12/2010 |
| WO | WO 2009/101128 | A1 | 8/2009 |

OTHER PUBLICATIONS

Maahs et alia. Low Plasma Adiponectin Levels Predict Progression of Coronary Artery Calcification. Circulation. Feb. 15, 2005;111(6):747-53. Epub Feb. 7, 2005.*

T. Callister et al., "Effect of HMG-CoA Reductase Inhibitors on Coronary Artery Disease as Assessed by Electron-Beam Computed Tomography," *New England Journal of Medicine*, vol. 339, No. 27, Dec. 31, 1998, pp. 1972-1978.

H-C Yoon et al., "Calcium Begets Calcium: Progression of Coronary Artery Calcification in Asymptomatic Subjects," *Radiology*, vol. 224, No. 1, Jul. 2002, pp. 236-241, published online before print.

R. Voss et al., "Prediction of risk of coronary events in middle-aged men in the Prospective Cardiovascular Münster Study (PROCAM) using neural networks," *International Journal of Epidemiology*, vol. 31, No. 6, Jul. 31, 2002, pp. 1253-1264.

P. Greenland et al., "Coronary Artery Calcium Score Combined with Framingham Score for Risk Prediction in Asymptomatic Individuals," *Journal of the American Medical Association*, vol. 291, No. 2, Jan. 14, 2004, pp. 210-215, correction in vol. 291, No. 5, Feb. 4, 2004, p. 563.

N. Wong et al., "Relation of Coronary Calcium Progression and Control of Lipids According to National Cholesterol Education Program Guidelines," *American Journal of Cardiology*, vol. 94, No. 4, Aug. 15, 2004, pp. 431-436.

J. Mieres et al., "Role of Noninvasive Testing in the Clinical Evaluation of Women with Suspected Coronary Artery Disease," *Circulation*, vol. 111, No. 5, Feb. 8, 2005, pp. 682-696, orginally published online Feb. 1, 2005.

A. Cassidy et al., "Progression of Subclinical Coronary Atherosclerosis: Does Obesity Make a Difference?," *Circulation*, vol. 111, No. 15, Apr. 19, 2005, pp. 1877-1882.

A. Taylor et al., "Coronary Calcium Independently Predicts Incident Premature Coronary Heart Disease over Measured Cardiovascular Risk Factors," *Journal of the American College of Cardiology*, vol. 46, No. 5, Sep. 6, 2005, pp. 807-814.

R. McClelland et al., "Distribution of Coronary Artery Calcium by Race, Gender, and Age: Results from the Multi-Ethnic Study of Atherosclerosis (MESA)," *Circulation*, vol. 113, No. 1, Jan. 3-10, 2006, pp. 30-37, orginally published online Dec. 19, 2005.

C. Twardy et al., "Epidemiological data mining of cardiovascular Bayesian networks," *electronic Journal of Health Informatics*, vol. 1, No. 1, 2006, e3, pp. 1-13.

A. Gopal et al., "Coronary calcium progression rates with a zero initial score by electron beam tomography," *International Journal of Cardiology*, vol. 117, No. 2, Apr. 25, 2007, pp. 227-231.

M. Budoff et al., "Long-Term Prognosis Associated with Coronary Calcification," *Journal of the American College of Cardiology*, vol. 49, No. 18, May 8, 2007, pp. 1860-1870.

R. Kronmal, et al., "Risk Factors for the Progression of Coronary Artery Calcification in Asymptomatic Subjects: Results from the Multi-Ethnic Study of Atherosclerosis (MESA)," *Circulation*, vol. 115, No. 21, May 29, 2007, pp. 2722-2730, orginally published online May 14, 2007.

J. Min et al., "Determinants of Coronary Calcium Conversion Among Patients With a Normal Coronary Calcium Scan: What is the 'Warranty Period' for Remaining Normal?" *Journal of the American College of Cardiology*, vol. 55, No. 11, Mar. 16, 2010, pp. 1110-1117.

T. Polonsky et al., "Coronary Artery Calcium Score and Risk Classification for Coronary Heart Disease Prediction," *Journal of the American Medical Association*, vol. 303, No. 16, Apr. 28, 2010, pp. 1610-1616.

Ch. Liapis et al., "Internal Carotid Artery Stenosis: Rate of Progression," *European Journal of Vascular and Endovascular Surgery*, vol. 19, No. 2, Feb. 2000, pp. 111-117.

T. Lumley et al., "A stroke prediction score in the elderly: validation and Web-based application," *Journal of Clinical Epidemiology*, vol. 55, No. 2, Feb. 2002, pp. 129-136.

J.S. Lee et al., "Development of a Stroke Prediction Model for Korean," *Journal of the Korean Neurological Association*, vol. 28, No. 1, Feb. 2010, pp. 13-21 (in Korean, with English abstract).

A. Khosla et al., "An Integrated Machine Learning Approach to Stroke Prediction," *Proceedings of the 16th ACM SIGKDD International Conference on Knowledge Discovery and Data Mining (KDD '10)*, pp. 183-192, conference held Jul. 25-28, 2010, Washington, DC.

K.S. Kim et al., "Association between Carotid Artery Intima-Media Thickness and Stroke Risk Factors in Ischemica Stroke," *Korean Journal of Stroke*, vol. 13, No. 3, Dec. 2011, pp. 129-133 (in Korean, with English abstract).

Non-Final Office Action mailed on Feb. 5, 2014, in U.S. Appl. No. 13/837,912 (12 pages, including attachments).

Non-Final Office Action mailed on Nov. 5, 2014, in U.S. Appl. No. 13/837,912 (6 pages, including attachment).

Non-Final Office Action mailed on Mar. 17, 2015, in U.S. Appl. No. 13/834,150 (19 pages, including attachments).

Final Office Action mailed on May 29, 2015, in U.S. Appl. No. 13/837,912 (11 pages, including attachment).

* cited by examiner

APPARATUS AND METHOD FOR PREDICTING POTENTIAL CHANGE OF CORONARY ARTERY CALCIFICATION (CAC) LEVEL

CROSS-REFERENCE TO RELATED APPLICATIONS

This application claims the benefit under 35 USC 119(a) of Korean Patent Application No. 10-2012-0026812 filed on Mar. 15, 2012, the entire disclosure of which is incorporated herein by reference for all purposes.

BACKGROUND

1. Field

The following description relates to technology for predicting a patient's potential change of Coronary Artery Calcification (CAC) level.

2. Description of Related Art

Coronary artery disease (CAD) is a leading cause of death in developed countries. About one-half of CAD patients experience myocardial infarction (MI) or acute myocardial infarction (AMI), and some of them die of MI or AMI.

A Coronary Artery Calcium Score (CACS) is closely related to heart diseases.

The CACS is obtained by means of computed tomography (CT) or another medical imaging process, and indicates progression of atherosclerosis and an accumulated amount of plaques in an artery. If a CACS increases, the chances that MI or heart diseases might occur are high.

For this reason, it is important for a patient, especially a high-risk patient, to have CACS measured to thereby be informed of a heart disease risk.

Reportedly, advanced age, current smoking, high blood pressure, diabetes, high cholesterol, low-density lipoprotein (LDL) cholesterol, high-density lipoprotein (HDL) cholesterol, obesity, and kidney disease are associated with an increase in CACS.

However, existing studies simply present statistical differences between a patient group and a healthy group on the basis of a risk factor, but fail to suggest a quantified risk degree of each risk factor, a collective effect of integrated risk factors, or an effective prediction model.

Furthermore, although various medical tests reflect newly-found risk factors in their results, the test results are not used to predict whether CACS would increase. That is, numerous studies simply help to predict occurrence of angina pectoris, MI, or cerebral infarction, which are heart diseases caused by an increased CACS.

SUMMARY

In one general aspect, an apparatus for predicting a potential change of a Coronary Artery Calcification (CAC) level includes a receiving unit configured to receive a patient's medical test data relating to CAC and corresponding operation information; a cluster determining unit configured to determine a cluster to which the patient's medical test data belong based on a characteristic of the patient; a risk factor score extracting unit configured to extract a risk factor score from the patient's medical test data; a prediction model storage unit configured to store a plurality of prediction models used for predicting a potential CAC level; a prediction model learning unit configured to perform machine learning by applying the extracted risk factor score to a prediction model corresponding to the determined cluster to which the patient's medical test data belong among the plurality of prediction models; and a predicting unit configured to obtain an outcome by applying the extracted risk factor score to the prediction model corresponding to the determined cluster to which the patient's medical test data belong.

The prediction model learning unit may be further configured to perform the machine learning when the operation information is a learning instruction; and the predicting unit may be further configured to obtain the outcome when the operation information is a predicting instruction.

The extracted risk factor score may include a Coronary Artery Calcification Score (CACS) and a corresponding measurement date.

The prediction model learning unit may be further configured to classify all CACSs into at least two sections; and each section of the at least two sections may be representative of a specific CAC level or a specific range of CAC levels.

The prediction model learning may be further configured to assign a first outcome to the patient's medical test data when a CAC level corresponding to a last measured CACS of the patient's medical test data is higher than a CAC level corresponding to a first measured CACS of the patient's medical test data; and assign a second outcome to the patient's medical test data in other cases.

When the predicting unit obtains the first outcome when the patient's medical test data is received with the predicting instruction, a CAC level of the patient may be predicted to increase; and when the predicting unit obtains the second outcome when the patient's medical test data is received with the predicting instruction, the CAC level of the patient may be predicted not to increase.

The extracted risk factor may include at least two Coronary Artery Calcification Score (CACS) scores; and the prediction model learning unit may be further configured to perform the machine learning using the at least two CACS scores.

In another general aspect, a method of predicting a potential change of a Coronary Artery Calcification (CAC) level includes receiving a patient's medical test data relating to CAC and corresponding operation information; determining a cluster to which the patient's medical test data belong based on a characteristic of the patient; extracting from the patient's medical test data a risk factor score of a risk factor of a risk factor set of the determined cluster to which the patient's medical test data belong; and selectively performing machine learning or performing prediction using a prediction model according to the operation information.

The selectively performing of the machine learning or performing the prediction using a prediction model may include, when the operation information is a learning instruction, performing the machine learning by applying the extracted risk factor score to a prediction model corresponding to the determined cluster to which the patient's medical test data belong among a plurality of prediction models; and, when the operation information is a predicting instruction, performing the prediction using a prediction model by applying the extracted risk factor score to the prediction model corresponding to the determined cluster to which the patient's medical test data belong.

The extracted risk factor score may include a Coronary Artery Calcification Score (CACS) and a corresponding measurement date.

The performing of the machine learning may include classifying all CACSs into at least two sections; and each section of the at least two sections may be representative of a specific CAC level or a specific range of CAC levels.

The performing of the machine learning may further include assigning a first outcome to the patient's medical test data when a CAC level corresponding to a last measured CACS of the patient's medical test data is higher than a CAC level corresponding to a first measured CACS of the patient's medical test data; and assigning a second outcome to the patient's medical test data in other cases.

When the performing of the prediction using a prediction model obtains the first outcome when the patient's medical test data is received with the predicting instruction, a CAC level of the patient may be predicted to increase; and when the performing of the prediction using a prediction model obtains the second outcome when the patient's medical test data is received with the predicting instruction, the CAC level of the patient may be predicted not to increase.

The determining of a cluster to which the patient's medical test data belong may include determining that the patient's medical test data belong to a first cluster when the patient's medical test data may include a Coronary Artery Calcification Score (CACS) of 0; and determining that the patient's medical test data belong to a second cluster when the patient's medical test data may include a CACS greater than 0.

In another general aspect, an apparatus for predicting a potential change of a Coronary Artery Calcification (CAC) level includes a receiving unit configured to receive a patient's medical test data relating to CAC; a cluster determining unit configured to determine a cluster to which the patient's medical test data belong based on a Coronary Artery Calcification Score (CACS) of the patient's medical test data; a risk factor score extracting unit configured to extract from the patient's medical test data a risk factor score of a risk factor of a risk factor set of the determined cluster to which the patient's medical test data belong; a prediction model storage unit configured to store a plurality of prediction models used for predicting a potential change of a CAC level; and a predicting unit configured to predict a potential change of a CAC level by applying the extracted risk factor score to a prediction model corresponding to the determined cluster to which the patient's medical test data belong among the plurality of prediction models.

If the patient's medical test data includes a CACS of 0, the risk factor set may include any one or any combination of an age, a blood pressure level, and a blood sugar level.

If the patient's medical test data includes a CACS greater than 0, the risk factor set may include any one or any combination of a CACS, an age, a blood pressure level, a blood sugar level, a body mass index (BMI) value, and a cholesterol level.

In another general aspect, a method of predicting a potential change of a Coronary Artery Calcification (CAC) level includes receiving a patient's medical test data relating to CAC; determining a cluster to which the patient's medical test data belong based on a Coronary Artery Calcification Score (CACS) of the patient's medical test data; extracting from the patient's medical test data a risk factor score of a risk factor of a risk factor set of the determined cluster to which the patient's medical test data belong; storing a plurality of prediction models used for predicting a potential change of a CAC level; and predicting a potential change of a CAC level by applying the extracted risk factor score to a prediction model corresponding to the determined cluster to which the patient's medical test data belong among the plurality of prediction models.

If the patient's medical test data includes a CACS of 0, the risk factor set may include any one or any combination of an age, a blood pressure level, and a blood sugar level.

If the patient's medical test data includes a CACS greater than 0, the risk factor set may include any one or any combination of a CACS, an age, a blood pressure level, a blood sugar level, a body mass index (BMI) value, and a cholesterol level.

Other features and aspects will be apparent from the following detailed description, the drawings, and the claims.

DETAILED DESCRIPTION

Figure 1:
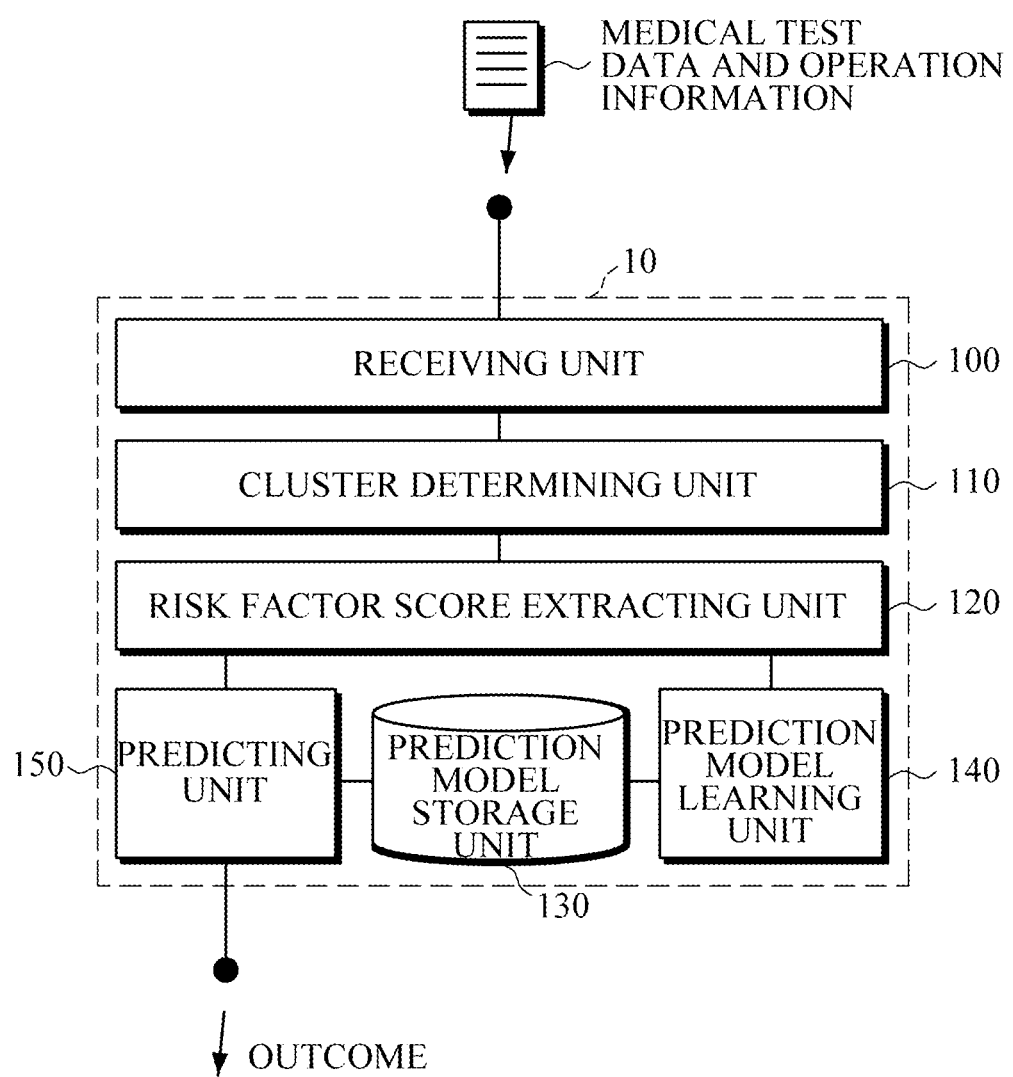
FIG. 1 is a block diagram illustrating an example of an apparatus for predicting a potential change of CAC level.

The following description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The following two conditions enable a potential change of a patient's Coronary Artery Calcification (CAC) level to be predicted.

First, a prediction model (a prediction model used for predicting a potential change of CAC level) needs to be learned for predicting a patient's potential change of CAC level based on data from various medical tests, including computed tomography (CT).

Second, an outcome indicative of a potential change of CAC level needs to be obtained by applying a specific patient's medical test data to the learned prediction model.

FIG. 1 is a block diagram illustrating an example of an apparatus for predicting a potential change of CAC level.

Referring to FIG. 1, the apparatus 10 for predicting a potential change of CAC level includes a receiving unit 100, a cluster determining unit 110, a risk factor score extracting unit 120, a prediction model storage unit 130, a prediction model learning unit 140, and a predicting unit 150.

The receiving unit 100 receives a patient's medical test data relating to CAC and corresponding operation information.

Medical test data is a collection of data about various medical tests and diagnoses with respect to a patient. A risk factor included in the medical test data may or may not be directly related to progression of CAC. Therefore, only a value of a risk factor (that is, a risk factor score) that has a profound statistical significance for progression of CAC should be selectively extracted and then applied to a prediction model for predicting a potential change of CAC level.

Operation information is an instruction that points out a type of an operation to be performed with respect to received medical test data. For example, the operation information may be an instruction that is input by selecting an appropriate operation button in a menu of the apparatus for predicting a patient's potential change of CAC level.

If the operation information is a learning instruction, the prediction model learning unit 140 performs machine learning using the medical test data. Alternatively, if the operation information is a predicting instruction, the predicting unit 150 predicts a patient's potential change of CAC level using the medical test data.

The cluster designating unit 110 determines a cluster to which a patient's medical test data belong based on at least one characteristic of the patient. The at least one characteristic of the patient may be included in the patient's medical test data.

A cluster is a collection of medical test data having a common characteristic. Thus, if a prediction model optimized for all of the medical test data belonging to the same cluster is used to perform a prediction based on new medical test data belonging to that cluster, prediction accuracy may improve profoundly.

For example, patients' medical test data may be classified into a plurality of clusters according to the patients' CACSs included in the patients' medical test data, and each cluster is representative of a specific CAC level or a specific range of CACS levels.

Table 1 below shows an example where patients' medical test data are classified into four CAC levels (or classes) using an Agatston score, a typical clustering algorithm for CAC levels.

TABLE 1

| | Class | | | |
|---|---|---|---|---|
| | Class I | Class II | Class III | Class IV |
| Section | CACS = 0 | 0 < CACS < 100 | 100 ≤ CACS < 400 | 400 ≤ CACS |
| Risk | Normal | Mild Risk | Intermediate Risk | High Risk |

Although Table 1 shows patients' medical test data being classified into four clusters respectively corresponding to Classes I, II, III, and IV, the following example will use a simplified case in which patients' medical test data are classified into two clusters consisting of one cluster corresponding to Class I and the other cluster corresponding to a combination of Classes II, III, and IV.

The risk factor score extracting unit 120 extracts from the medical test data at least one risk factor score of a risk factor of a risk factor set of the determined cluster to which the medical test data belong.

A risk factor is a factor that influences a potential change of CAC level. For example, a patient's first measured CACS or CAC level, a blood pressure level, and a cholesterol level are highly significant risk factors. A value of a risk factor, that is, a risk factor score, is included in the medical test data. For example, if a risk factor is age, a patient's age (for example, 30) is included in the medical test data as a risk factor score. A different risk factor set may be applied to each prediction model.

Table 2 below shows an example of a format of a risk factor set applied to a prediction model.

TABLE 2

| Risk Factor Set | Model | Risk Factor | OR | CI (95%) | | P-Value |
|---|---|---|---|---|---|---|
| $RFS_1$ | $Model_1$ | $RF_1$ | 1.01 | 1.01 | 1.01 | 3.54E−07 |
| | | $RF_2$ | 0.13 | 0.11 | 0.15 | <2E−16 |
| | | ... | ... | ... | ... | ... |
| ... | ... | ... | ... | ... | ... | ... |

A risk factor set $RFS_1$ shown in Table 2 consists of a plurality of risk factors $RF_1$, $RF_2$, . . . . Among the factors included in each medical test data, a factor closely related to progression of CAC is used as a risk factor. For example, a risk factor set may include a value of a significant risk factor, such as a first measured CACS, a blood pressure level, an age, a value determined according to whether the patient is a smoker or a non-smoker, a value determined according to whether the patient has diabetes, a LDL cholesterol level, and an HDL cholesterol level.

Each risk factor may include additional fields to show an odds ratio (OR) between the risk factor and a progression of CAC, a confidence interval of the OR (for example, a confidence level of 95%), and a statistical significance (P-Value) of the OR.

The prediction model storage unit 130 stores a plurality of prediction models used for predicting a potential change of CAC level.

A different prediction model is employed with respect to each cluster. Therefore, if there are a plurality of clusters, a plurality of corresponding prediction models are provided. The plurality of prediction models are stored in the prediction model storage unit 130. In addition, if an operation is performed with respect to medical test data belonging to a specific cluster, a prediction model corresponding to the specific cluster is selected to be used.

The prediction model learning unit 140 performs machine learning by applying the risk factor score extracted by the risk factor score extracting unit 120 to the prediction model corresponding to the specific cluster to which the medical test data belong.

A wide range of machine learning algorithms may be used to perform machine learning on each prediction model. For example, a support vector machine (SVM), a decision tree, a multilayer perceptron (MLP), a LogitBoost, or any other machine learning algorithm known to one of ordinary skill in the art, or any combination thereof may be used.

A prediction model may be learned with respect to a patient's medical test data by receiving the medical test data and then performing machine learning on the prediction model using a specific algorithm. Next, if a patient's new medical test data is received, the prediction model may be employed to predict the patient's potential change of CAC level based on the new medical test data.

The predicting unit 150 obtains an outcome indicative of the patient's potential change of CAC level by applying a risk factor score extracted from the medical test data by the risk factor extracting unit 120 to a prediction model corresponding to the cluster to which the medical test data belong.

Figure 2:
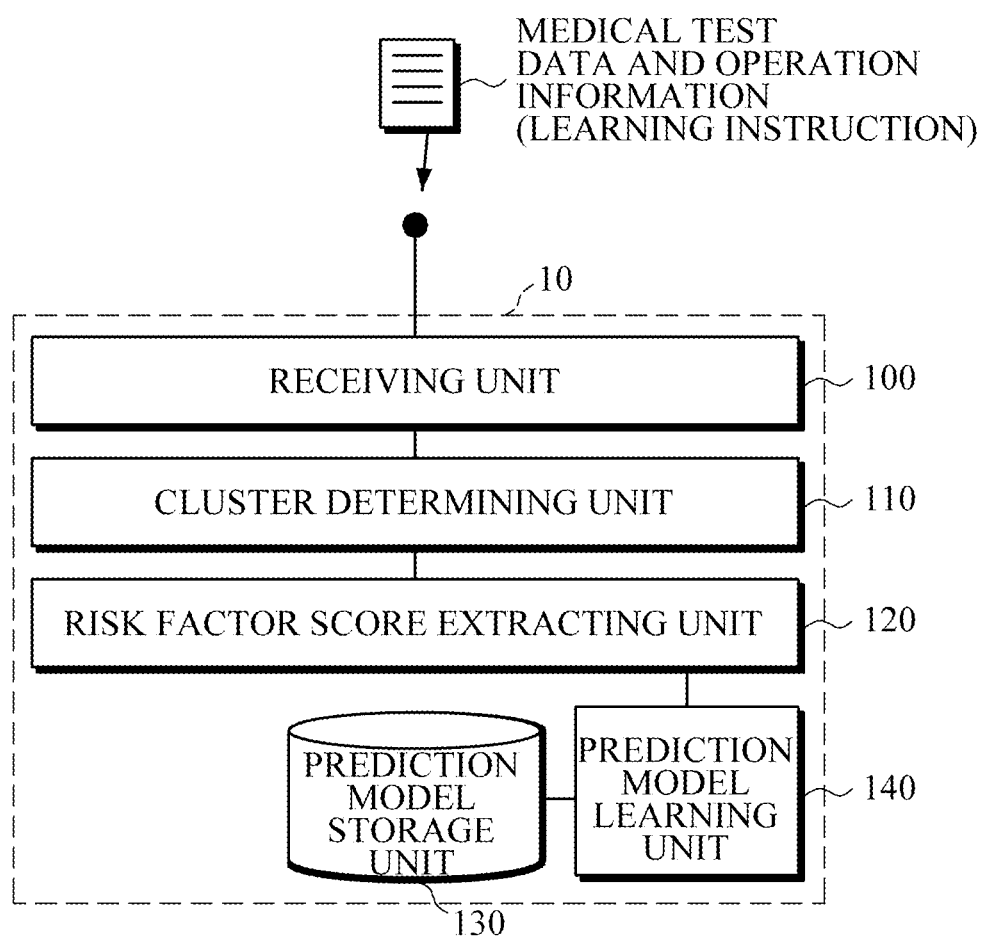
FIG. 2 is a block diagram illustrating an example of elements of the apparatus for predicting a potential change of CAC level shown in FIG. 1 that are activated when operation information is a learning instruction.
Figure 3:
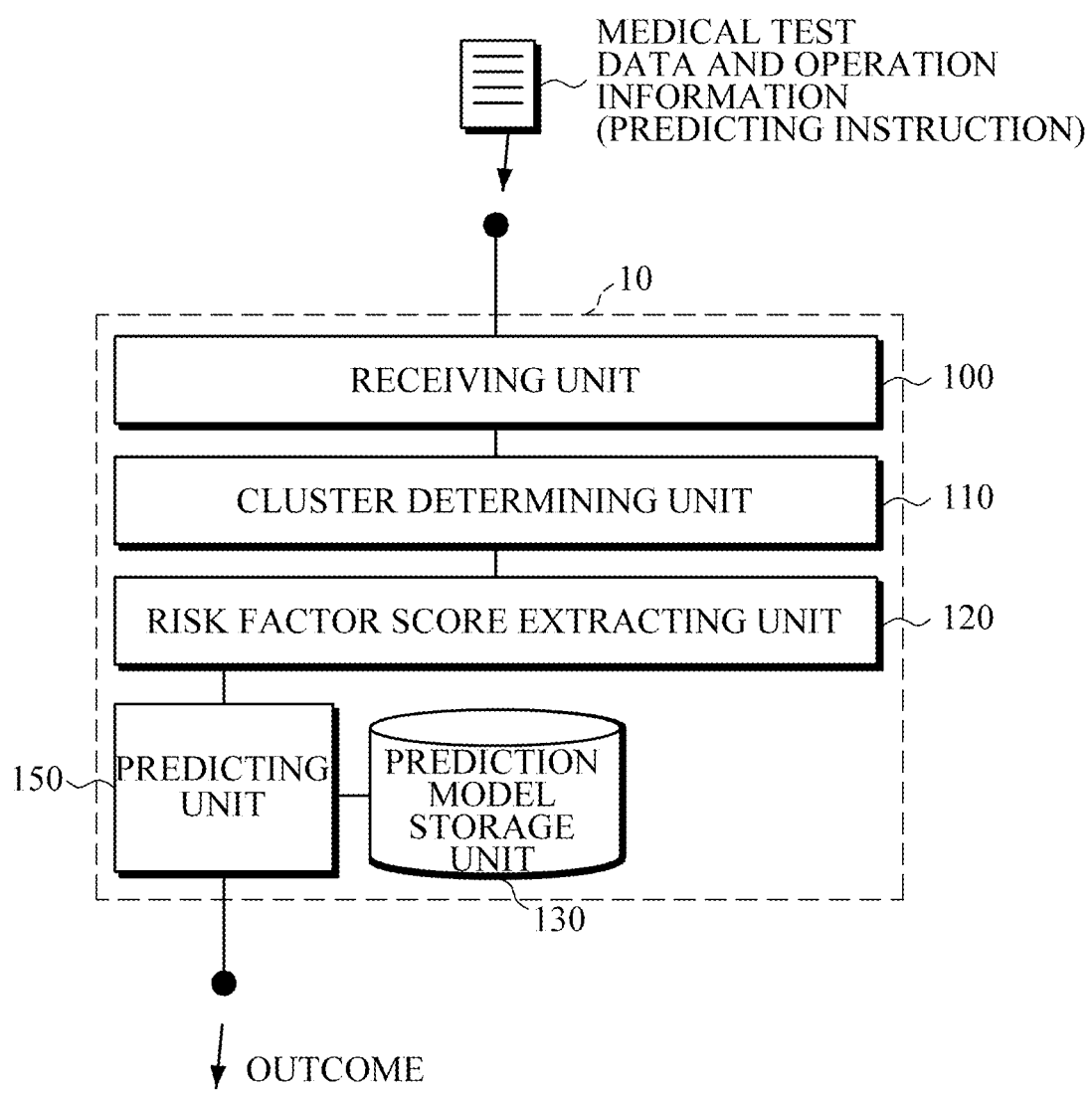
FIG. 3 is a block diagram illustrating an example of elements of the apparatus for predicting a potential change of CAC level shown in FIG. 1 that are activated when operation information is a predicting instruction.

When medical test data is received in the apparatus 10 for predicting a potential change of CAC level shown in FIG. 1, the medical test data may used to perform machine learning on a corresponding prediction model or to predict a potential change of CAC level. FIGS. 2 and 3 illustrate each of these cases.

FIG. 2 is a diagram illustrating an example of elements of the apparatus 10 for predicting a potential change of CAC level shown in FIG. 1 that are activated when operation information is a learning instruction.

If operation information is a learning instruction, elements of the apparatus 10 for predicting a potential change of CAC level that are used in performing machine learning on a prediction model using received medical test data are activated. These elements include the receiving unit 100, the cluster determining unit 110, the risk factor score extracting unit 120, the prediction model storage unit 130, and the prediction model learning unit 140 as shown in FIG. 2.

FIG. 3 is a diagram illustrating an example of elements of the apparatus 10 for predicting a CAC level shown in FIG. 1 that are activated when operation information is a predicting instruction.

If operation information is a predicting instruction, elements of the apparatus 10 for predicting a potential change of CAC level that are used in predicting a potential change of CAC level by applying received medical test data to a prediction model corresponding to a cluster to which the medical test data belong are activated. These elements include the receiving unit 100, the cluster determining unit 110, the risk factor score extracting unit 120, the prediction model storage unit 130, and the prediction model learning unit 140 as shown in FIG. 3.

Figure 4:
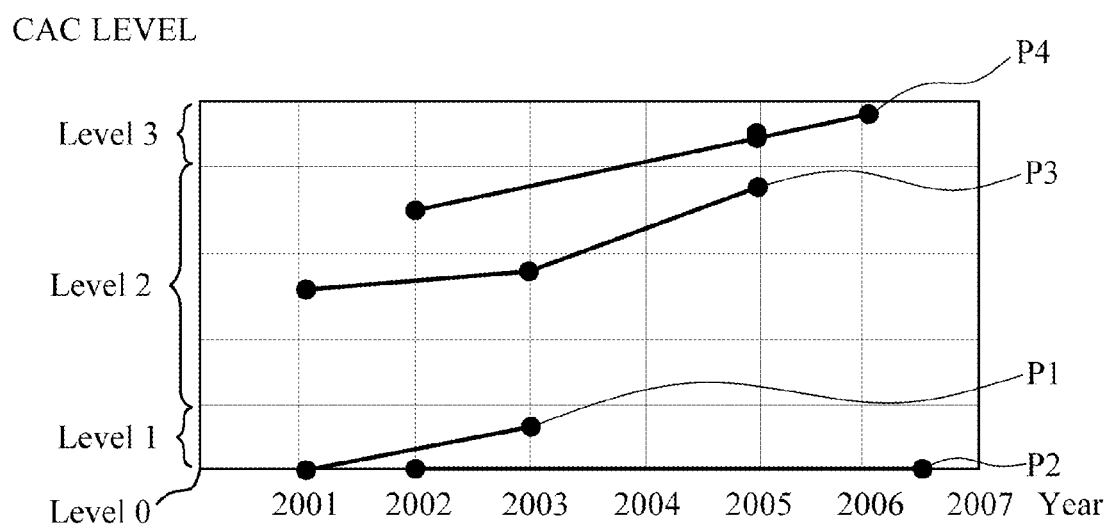
FIG. 4 is a graph for explaining an example of a progression of CAC in phases.

FIG. 4 is a graph for explaining a progression of CAC in phases.

A progression or a state of CAC may be represented by a value or a section. A diagnosis environment or a patient's condition and other characteristics may cause deviation among patients' medical test data, so it may be more accurate to describe progression of CAC in phases.

Referring to FIG. 4, a patient P1 was tested to measure a CACS in 2001 and 2003, a patient P2 was tested to measure a CACS in 2002 and 2006, a patient P3 was tested to measure a CACS in 2001, 2003, and 2005, and a patient P4 was tested to measure a CACS in 2002, 2005, and 2006.

A CAC level in FIG. 4 corresponds to a class in Table 1. That is, CAC level 0 indicates a normal state (Class I), CAC level 1 indicates a mild risk (Class II), CAC level 2 indicates an intermediate risk (Class III), and CAC level 3 indicates a high risk (Class IV).

A CACS and a corresponding measurement date are risk factors that may be used for performing machine learning on a prediction model and employing the learned prediction model to predict a potential change of CAC level.

Specifically, a prediction model should be learned first. If at least two factor scores, each including a CACS and a corresponding measurement date, are extracted from medical test data, machine learning may be performed on a prediction model by applying the first measured CACS and the last measured CACS, along with other risk factor scores included in the medical test data, to the prediction model corresponding to a cluster to which the medical test data belong.

Next, a potential change of CAC level is predicted using the learned prediction model. If along with other risk factors, a CACS and a corresponding measurement date included in medical test data are input to the learned prediction model, an outcome indicative of a potential change of CAC level that might occur at a specific point in time may be obtained. The specific point in time may be, for example, four years in the future. However, four years is merely one example, and other time periods may be used.

Table 3 below shows the difference between the first measured CAC level and the last measured CAC level of the patients shown in FIG. 4.

TABLE 3

| Patient | CAC Level at First Measurement | CAC Level at Last Measurement | Level Change |
|---|---|---|---|
| P1 | Level 0 | Level 1 | Increase (+1) |
| P2 | Level 0 | Level 0 | No Change (±0) |
| P3 | Level 2 | Level 2 | No Change (±0) |
| P4 | Level 2 | Level 3 | Increase (+1) |

Referring again to FIG. 1, the prediction model learning unit 140 determines whether a CAC level corresponding to the last measured CACS is higher than a CAC level corresponding to the first measured CACS in a patient's medical test data. For example, in the case of the patients P1 and P4, the CAC level corresponding to the last measured CACS is higher than the CAC level corresponding to first measured CACS. In contrast, in the case of the patients P2 and P3, the CAC level corresponding to the last measured CACS is the same as the CAC level corresponding to first measured CACS.

The fact that a CAC level has increased for the patients P1 and P4 indicates that a progression of CAC has become worse. In this case, the prediction model learning unit 140 may assign "1" as an outcome indicating information about a potential change of CAC level.

Alternatively, the fact that a CAC level has not increased for patients P2 and P3 indicates that the CAC level has been maintained at a relatively constant level or that CAC has been reduced or eliminated. In this case, the prediction model learning unit 140 may assign "0" as an outcome indicating information about a potential change of CAC level.

As such, if machine learning is performed on a prediction model by the prediction model learning unit 140 using medical test data, the prediction model may be employed to predict a potential change of CAC level for different medical test data belonging to the same cluster as the medical test data used to perform the machine learning.

That is, if the predicting unit 150 obtains an outcome of "1" when a patient's medical test data is received with a predicting instruction, the patient's potential CAC level is predicted to increase. For example, if a CACS included in received medical test data corresponds to CAC Level 1 indicating "mild risk", a potential CAC level is predicted to become CAC Level 2 indicating "intermediate risk".

In contrast, if the predicting unit 150 obtains an outcome of "0" when a patient's medical test data is received with a predicting instruction, the patient's potential CAC level is predicted not to increase. For example, if a CACS included in received medical test data corresponds to CAC Level 2 indicating "intermediate risk", a potential CAC level is predicted to remain at CAC Level 2 indicating "intermediate risk".

Machine learning is performed on a prediction model only when medical test data is a result of two or more CAC diagnoses. If a CAC diagnosis has not been performed, or has been performed only once, it is impossible to extract a first measured CACS and a last measured CACS from the medical test data because a CACS either has not been measured at all, or has been measured only once.

In the above example, patients are classified into two clusters (one cluster corresponding to Class I and the other cluster corresponding to a combination of Classes II, III, and IV), but this is merely one example. In other words, patients' medical test data may be clustered in various ways with a variety of existing clustering techniques.

However, there may be numerous standards reflecting a common characteristic between all of the medical test data belonging to the same cluster, and how to apply each of the standards (or a combination of the standards) may determine a type of a clustering technique to be used.

For example, if a range of a CAC level is a clustering standard, the range may be widened or narrowed, or a greater or fewer number of clusters may be used.

Figure 5:
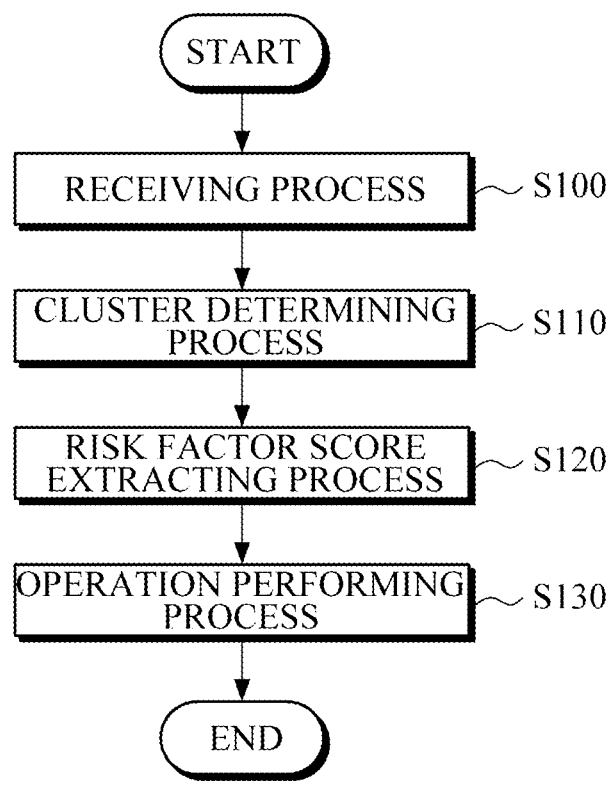
FIG. 5 is a flow chart illustrating an example of a method of predicting a CAC level.

FIG. 5 is a flow chart illustrating an example of a method of predicting a potential change of CAC level. Referring to FIG. 5, the method of predicting a potential change of CAC level includes a receiving process S100, a cluster determining process S110, a risk factor score extracting process S120, and an operation performing process S130.

In the receiving process S100, a patient's medical test data relating to CAC and corresponding operation information are received in an apparatus for predicting a potential change of CAC level.

In the cluster determining process S110, clustering is performed on the medical test data received in the receiving process S100 based on at least one characteristic of the patient. The at least one characteristic of the patient may be included in the medical test data. Accordingly, a cluster to which the medical test data belong is determined.

For example, if medical test data are classified into two clusters based on a CACS as a characteristic of the patient, received medical test data with a normal CAC level (that is, CACS=0) may belong to a cluster corresponding to Class I, and received medical test data with an abnormal CAC level (that is, CACS>0) may belong to a cluster corresponding to a combination of Classes II, III, and IV.

In the risk factor score extracting process S120, at least one risk factor score of a risk factor of a risk factor set of the cluster to which the medical test data belong is extracted from the medical test data.

In the operation performing process S130, machine learning or prediction is selectively performed based on the operation information that was received in the receiving process S100.

Figure 6:
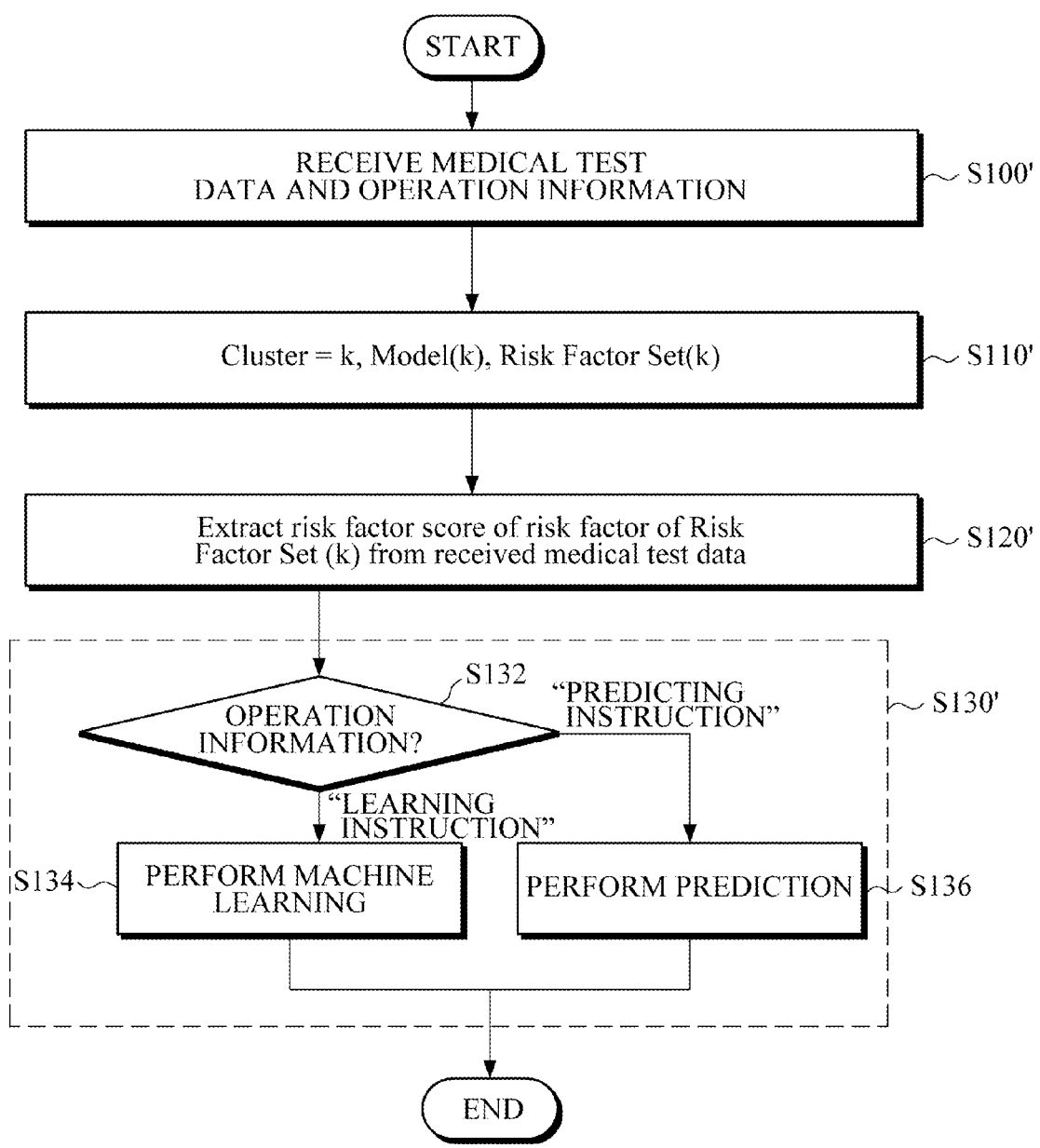
FIG. 6 is a flow chart illustrating a detailed example of the method of FIG. 5.

FIG. 6 is a flow chart illustrating a detailed example of the method of FIG. 5. Processes S100', S110', S120', and S130' of FIG. 6 respectively correspond to processes S100, S110, S120, and S130 of FIG. 5.

In a receiving process S100', a patient's medical test data and corresponding operation information are received in a receiving unit of an apparatus for predicting a potential change of CAC level.

In a cluster determining process S110', a cluster to which the medical test data belong is determined based on at least one characteristic of the patient. The at least one characteristic of the patient may be included in the medical test data. In addition, a prediction model to be used with respect to the medical test data is determined.

For example, in the case where a clustering technique requiring N clusters ($1<k\leq N$) is used and the received medical test data belong to a k-th cluster, a prediction model Model (k) and a risk factor set Risk Factor Set (k) each corresponding to the k-th cluster are used. The Risk Factor Set (k) is a set of risk factors of the medical test data of the k-th cluster.

In a risk factor score extracting process S120', a risk factor score of a risk factor of the Risk Factor Set (k) is extracted from the received medical test data. Different prediction models and different risk factor sets are used with respect to medical test data belonging to different clusters. Conversely, the same prediction model and the same risk factor set are used with respect to medical test data belonging to the same cluster.

An operation performing process S130' includes an operation information determining process S132.

When the operation information is a "learning instruction", the risk factor score extracted in the process S120' for extracting a risk factor score is applied to the prediction model corresponding to a cluster to which the received medical test data belong to perform machine learning on the prediction model in a machine learning process S134.

When the operation information is a "predicting instruction", the risk factor score extracted in the risk factor score extracting process S120' is applied to a prediction model corresponding to the cluster to which the received medical test data belong to predict a patient's potential change of CAC level in a predicting process S136. The potential change of CAC level may be predicted at a specific point in time, for example, four years in the future. However, four years is merely one example, and other time periods may be used.

If CAC levels are used to show a progression of CAC, a CAC level corresponding to a last measured CACS is compared with a CAC level corresponding to a first measured CACS in the machine learning process S134. If the CAC level corresponding to the last measured CACS is higher than the CAC level corresponding to the first measured CAC level, an outcome (for example, "1") indicating that a CAC level is predicted to increase may be assigned. If not, an outcome (for example, "0") indicating that a CAC level is not predicted to increase may be assigned.

If machine learning is performed on a prediction model in the machine learning process S134 based on medical test data as described above, the prediction model may be used to perform prediction with respect to different medical test data to thereby predict a potential change of CAC level according to an outcome.

For example, if an outcome of "1" is obtained with respect to the different medical test data in the predicting process S136, it may be predicted that a CAC level will increase. Alternatively, if an outcome of "0" is obtained with respect to the different medical test data, it may be predicted that a CAC level will not increase.

Figure 7:
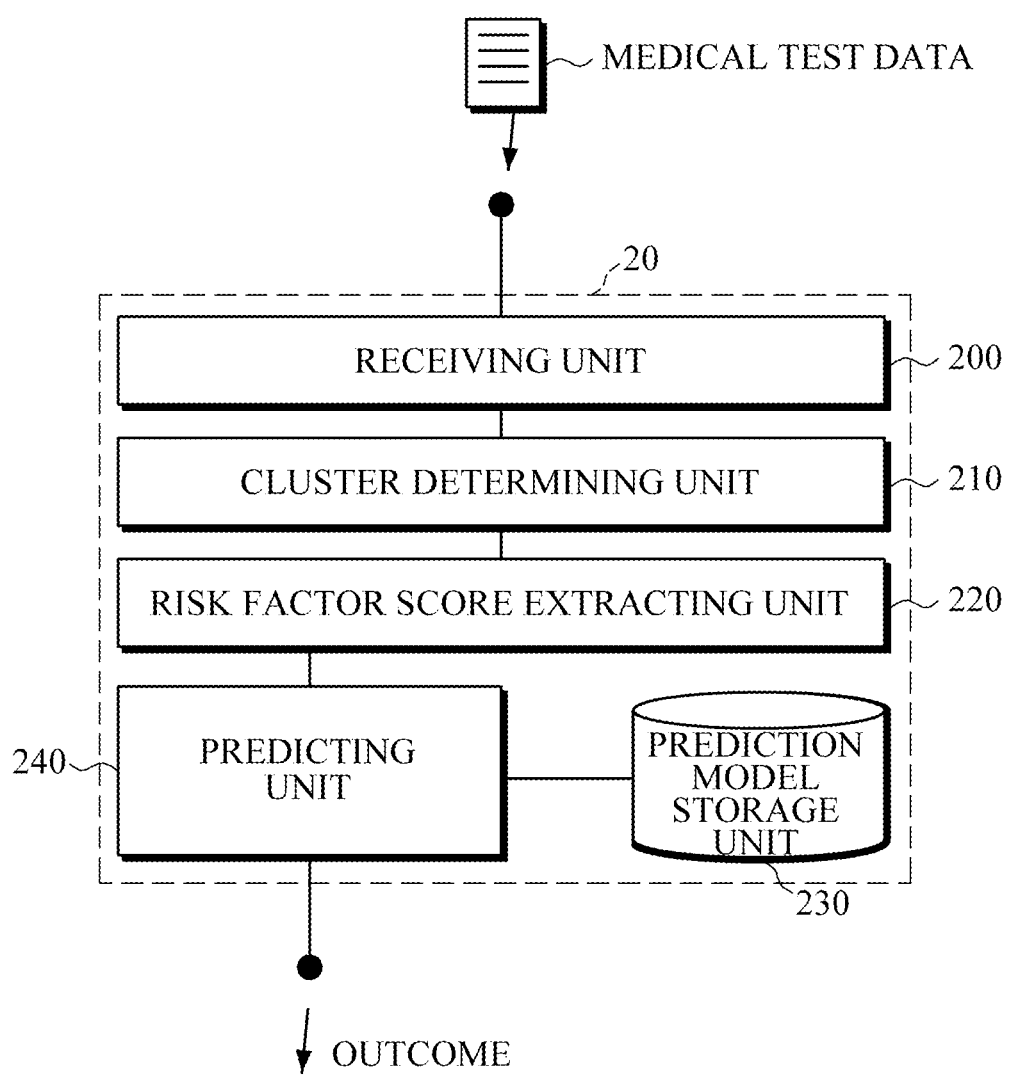
FIG. 7 is a block diagram illustrating another example of an apparatus for predicting a potential change of CAC level.

FIG. 7 is a block diagram illustrating another example of an apparatus for predicting a potential change of CAC level. Referring to FIG. 7, the apparatus 20 for predicting a potential change of CAC level does not perform learning on a plurality of prediction models stored in a prediction model storage unit.

A receiving unit 200 receives a patient's medical test data relating to CAC. Since machine learning on a prediction model is not performed in the apparatus 20 for predicting a potential change of CAC level, it is not necessary to receive operation information.

A cluster determining unit 210 determines a cluster to which the received medical test data belong based on a CACS. The CACS may be included in the medical test data.

A risk factor score extracting unit 220 extracts from the medical test data at least one risk factor score of a risk factor of a risk factor set of the determined cluster to which the medical test data belong.

If the medical test data belong to a cluster characterized by a CAC level of 0, a risk factor set of the cluster includes any one or any combination of an age, a blood pressure level, and a blood sugar level. Other risk factors affecting a potential change of CAC level may also be included in the risk factor set.

Alternatively, if the medical test data belong to a cluster characterized by a CACS greater than 0, a risk factor set of the cluster includes any one or any combination of a CACS, an age, a blood pressure level, a blood sugar level, a BMI value, and a cholesterol level. Other risk factor scores affecting a potential change of CAC level may also be included in the risk factor set.

The prediction model storage unit 230 stores a plurality of prediction models used for predicting a potential change of CAC level.

The predicting unit 240 obtains an outcome by applying the at least one risk factor score extracted from the medical test data by the risk factor score extracting unit 220 to a prediction model corresponding to the determined cluster to which the medical test data belong.

If the predicting unit 240 obtains an outcome of "1" discussed above in connection with the examples in FIGS. 1 and 6, this indicates that the patient's potential CAC level is predicted to increase. Conversely, if the predicting unit 240 obtains an outcome of "0" discussed above in connection with the examples in FIGS. 1 and 6, this indicates that the patient's potential CAC level is predicted to not increase.

As described above, if it is possible to predict whether a patient's potential CAC level will increase at a specific point in time (for example, four years in the future), high-risk patients may be appropriately treated with medication so that heart diseases, strokes, and other cardiovascular problems may be effectively prevented. In addition, the prediction may help low-risk patients avoid unnecessary medical tests and excessive preventive treatment.

The receiving unit 100, the cluster determining unit 110, the risk factor score extracting unit 120, the prediction model storage unit 130, the prediction model learning unit 140, the predicting unit 150, the receiving unit 200, the cluster determining unit 210, the risk factor score extracting unit 220, the prediction model storage unit 230, and the predicting unit 240 described above that perform the operations illustrated in FIGS. 5 and 6 may be implemented using one or more hardware components, one or more software components, or a combination of one or more hardware components and one or more software components.

A hardware component may be, for example, a physical device that physically performs one or more operations, but is not limited thereto. Examples of hardware components include resistors, capacitors, inductors, power supplies, frequency generators, operational amplifiers, power amplifiers, low-pass filters, high-pass filters, band-pass filters, analog-to-digital converters, digital-to-analog converters, and processing devices.

A software component may be implemented, for example, by a processing device controlled by software or instructions to perform one or more operations, but is not limited thereto. A computer, controller, or other control device may cause the processing device to run the software or execute the instructions. One software component may be implemented by one processing device, or two or more software components may be implemented by one processing device, or one software component may be implemented by two or more processing devices, or two or more software components may be implemented by two or more processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

A processing device configured to implement a software component to perform an operation A may include a processor programmed to run software or execute instructions to control the processor to perform operation A. In addition, a processing device configured to implement a software component to perform an operation A, an operation B, and an operation C may have various configurations, such as, for example, a processor configured to implement a software component to perform operations A, B, and C; a first processor configured to implement a software component to perform operation A, and a second processor configured to implement a software component to perform operations B and C; a first processor configured to implement a software component to perform operations A and B, and a second processor configured to implement a software component to perform operation C; a first processor configured to implement a software component to perform operation A, a second processor configured to implement a software component to perform operation B, and a third processor configured to implement a software component to perform operation C; a first processor configured to implement a software component to perform operations A, B, and C, and a second processor configured to implement a software component to perform operations A, B, and C, or any other configuration of one or more processors each implementing one or more of operations A, B, and C. Although these examples refer to three operations A, B, C, the number of operations that may implemented is not limited to three, but may be any number of operations required to achieve a desired result or perform a desired task.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

Functional programs, codes, and code segments for implementing the examples disclosed herein can be easily constructed by a programmer skilled in the art to which the examples pertain based on the drawings and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for predicting a potential change of a Coronary Artery Calcification (CAC) level, the apparatus comprising:
    a receiving processor configured to receive a patient's medical test data relating to CAC and corresponding operation information;
    a cluster determining processor configured to determine a cluster to which the patient's medical test data belong based on a characteristic of the patient;
    a risk factor score extracting processor configured to extract a risk factor score from the patient's medical test data;
    a prediction model storage processor configured to store a plurality of prediction models used for predicting a potential CAC level;
    a prediction model learning processor configured to perform machine learning by applying the extracted risk factor score to a prediction model corresponding to the determined cluster to which the patient's medical test data belong among the plurality of prediction models; and
    a predicting processor configured to obtain an outcome by applying the extracted risk factor score to the prediction model corresponding to the determined cluster to which the patient's medical test data belong,
    wherein the extracted risk factor score comprises a Coronary Artery Calcification Score (CACS) and a corresponding measurement date,
    wherein the prediction model learning processor is further configured to classify all CACSs into at least two sections; and
    each section of the at least two sections is representative of a specific CAC level or a specific range of CAC levels, and
    wherein the prediction model learning processor is further configured to:
    assign a first outcome to the patient's medical test data when a CAC level corresponding to a last measured CACS of the patient's medical test data is higher than a CAC level corresponding to a first measured CACS of the patient's medical test data; and
    assign a second outcome to the patient's medical test data in other cases.

2. The apparatus of claim 1, wherein the prediction model learning processor is further configured to perform the machine learning when the operation information is a learning instruction; and
    the predicting processor is further configured to obtain the outcome when the operation information is a predicting instruction.

3. The apparatus of claim 1, wherein when the predicting processor obtains the first outcome when the patient's medical test data is received with the predicting instruction, a CAC level of the patient is predicted to increase; and
    when the predicting processor obtains the second outcome when the patient's medical test data is received with the predicting instruction, the CAC level of the patient is predicted not to increase.

4. The apparatus of claim 1, wherein the extracted risk factor comprises at least two Coronary Artery Calcification Score (CACS) scores; and
    the prediction model learning processor is further configured to perform the machine learning using the at least two CACS scores.

5. A method of predicting a potential change of a Coronary Artery Calcification (CAC) level, the method comprising:
    receiving a patient's medical test data relating to CAC and corresponding operation information;
    determining a cluster to which the patient's medical test data belong based on a characteristic of the patient;
    extracting from the patient's medical test data a risk factor score of a risk factor of a risk factor set of the determined cluster to which the patient's medical test data belong; and
    selectively performing machine learning or performing prediction using a prediction model according to the operation information,
    wherein the extracted risk factor score comprises a Coronary Artery Calcification Score (CACS) and a corresponding measurement date, and
    wherein the performing of the machine learning comprises classifying all CACSs into at least two sections; and
    each section of the at least two sections is representative of a specific CAC level or a specific range of CAC levels, and
    wherein the performing of the machine learning further comprises:
    assigning a first outcome to the patient's medical test data when a CAC level corresponding to a last measured CACS of the patient's medical test data is higher than a CAC level corresponding to a first measured CACS of the patient's medical test data; and
    assigning a second outcome to the patient's medical test data in other cases.

6. The method of claim 5, wherein the selectively performing of the machine learning or performing the prediction using a prediction model comprises:
    when the operation information is a learning instruction, performing the machine learning by applying the extracted risk factor score to a prediction model corresponding to the determined cluster to which the patient's medical test data belong among a plurality of prediction models; and when the operation information is a predicting instruction, performing the prediction using a prediction model by applying the extracted risk factor score to the prediction model corresponding to the determined cluster to which the patient's medical test data belong.

7. The method of claim 5, wherein when the performing of the prediction using a prediction model obtains the first outcome when the patient's medical test data is received with the predicting instruction, a CAC level of the patient is predicted to increase; and when the performing of the prediction using a prediction model obtains the second outcome when the patient's medical test data is received with the predicting instruction, the CAC level of the patient is predicted not to increase.

8. The method of claim 5, wherein the determining of a cluster to which the patient's medical test data belong comprises:

determining that the patient's medical test data belong to a first cluster when the patient's medical test data comprises a Coronary Artery Calcification Score (CACS) of 0; and determining that the patient's medical test data belong to a second cluster when the patient's medical test data comprises a CACS greater than 0.

9. An apparatus for predicting a potential change of a Coronary Artery Calcification (CAC) level, the apparatus comprising:

a receiving processor configured to receive a patient's medical test data relating to CAC;

a cluster determining processor configured to determine a cluster to which the patient's medical test data belong based on a Coronary Artery Calcification Score (CACS) of the patient's medical test data;

a risk factor score extracting processor configured to extract from the patient's medical test data a risk factor score of a risk factor of a risk factor set of the determined cluster to which the patient's medical test data belong;

a prediction model storage processor configured to store a plurality of prediction models used for predicting a potential change of a CAC level; and a predicting processor configured to predict a potential change of a CAC level by applying the extracted risk factor score to a prediction model corresponding to the determined cluster to which the patient's medical test data belong among the plurality of prediction models, wherein the extracted risk factor score comprises a Coronary Artery Calcification Score (CACS) and a corresponding measurement date, wherein the prediction model learning processor is further configured to classify all CACSs into at least two sections; and each section of the at least two sections is representative of a specific CAC level or a specific range of CAC levels, and wherein the prediction model learning processor is further configured to:

assign a first outcome to the patient's medical test data when a CAC level corresponding to a last measured CACS of the patient's medical test data is higher than a CAC level corresponding to a first measured CACS of the patient's medical test data; and assign a second outcome to the patient's medical test data in other cases.

10. The apparatus of claim 9, wherein if the patient's medical test data comprises a CACS of 0, the risk factor set comprises any one or any combination of an age, a blood pressure level, and a blood sugar level.

11. The apparatus of claim 9, wherein if the patient's medical test data comprises a CACS greater than 0, the risk factor set comprises any one or any combination of a CACS, an age, a blood pressure level, a blood sugar level, a body mass index (BMI) value, and a cholesterol level.

12. A method of predicting a potential change of a Coronary Artery Calcification (CAC) level, the method comprising:

receiving a patient's medical test data relating to CAC;

determining a cluster to which the patient's medical test data belong based on a Coronary Artery Calcification Score (CACS) of the patient's medical test data;

extracting from the patient's medical test data a risk factor score of a risk factor of a risk factor set of the determined cluster to which the patient's medical test data belong;

storing a plurality of prediction models used for predicting a potential change of a CAC level; and predicting a potential change of a CAC level by applying the extracted risk factor score to a prediction model corresponding to the determined cluster to which the patient's medical test data belong among the plurality of prediction models, wherein the extracted risk factor score comprises a Coronary Artery Calcification Score (CACS) and a corresponding measurement date, and wherein the performing of the machine learning comprises classifying all CACSs into at least two sections; and each section of the at least two sections is representative of a specific CAC level or a specific range of CAC levels, and wherein the performing of the machine learning further comprises:

assigning a first outcome to the patient's medical test data when a CAC level corresponding to a last measured CACS of the patient's medical test data is higher than a CAC level corresponding to a first measured CACS of the patient's medical test data; and assigning a second outcome to the patient's medical test data in other cases.

13. The method of claim 12, wherein if the patient's medical test data comprises a CACS of 0, the risk factor set comprises any one or any combination of an age, a blood pressure level, and a blood sugar level.

14. The method of claim 12, wherein if the patient's medical test data comprises a CACS greater than 0, the risk factor set comprises any one or any combination of a CACS, an age, a blood pressure level, a blood sugar level, a body mass index (BMI) value, and a cholesterol level.

* * * * *